United States Patent [19]

Ledis et al.

[11] Patent Number: 4,485,175
[45] Date of Patent: Nov. 27, 1984

[54] METHOD FOR THREE-VOLUME DIFFERENTIAL DETERMINATION OF LYMPHOCYTE, MONOCYTE AND GRANULOCYTE POPULATIONS OF LEUKOCYTES

[75] Inventors: Stephen L. Ledis, Hialeah; Ted Sena, Miami; Harold R. Crews, Pembroke Pines; James H. Carter, II, Ft. Lauderdale, all of Fla.

[73] Assignee: Coulter Electronics, Inc., Hialeah, Fla.

[21] Appl. No.: 454,926

[22] Filed: Jan. 3, 1983

[51] Int. Cl.$^3$ ............... G01N 33/48; G01N 33/72
[52] U.S. Cl. ................................. 436/63; 436/10; 436/17
[58] Field of Search ..................... 436/63, 10, 17

[56] References Cited

U.S. PATENT DOCUMENTS

| | | | |
|---|---|---|---|
| 3,874,852 | 4/1975 | Hamill | 23/230 |
| 4,213,876 | 7/1980 | Crews et al. | 252/408 |
| 4,286,963 | 9/1983 | Ledis et al. | 23/230 |
| 4,346,018 | 8/1982 | Carter et al. | 252/408 |

OTHER PUBLICATIONS

Nicol, D. J. et al., J. Clinical Pathology, (1971), 24, p. 882.
Davis, R. E. et al., J. Med. Lab. Techol. (1969), 26, 26–29.
Barnard, D. F. et al., J. Clin. Path., 22, Suppl. Coll. Path, (1969), 3, 26–33.
Ballard, B. C. D., J. Clin. Path., 25, p. 460, (1972).
Hatch et al., Am. J. Clin. Path., 36, 220–223, (1961).
Armak Arquad, 81-6, Bulletin.
J. M. England et al., Lancet, Mar. 1, 1975, p. 492.
J. M. England et al., Lancet, May 22, 1976, p. 1143.
J. M. England et al., J. Clin. Path., 27, 623, (1974).
P. A. Wycherly and M. J. O'Shea, J. Clin. Path., 31, p. 271, (1978).
D'Angelo et al., J. Clin. Path., 38, No. 6, 658–662.

*Primary Examiner*—Arnold Turk
*Attorney, Agent, or Firm*—Meredith P. Sparks; Gerald R. Hibnick

[57] ABSTRACT

A method and reagent system is described for differential determination of three-populations of leukocytes (lymphocyte, monocyte and granulocyte), using an automatic counting system. The reagent system includes a blood diluent and lysing reagent. The blood diluent is an osmotically balanced aqueous solution of ingredients at a preselected pH for maintaining erythrocyte morphology, blood cell stabilizing, buffering and bacteriostatic action. The lysing reagent is a mixture of an aqueous solution of quaternary ammonium salts, which lysing reagent is added to the diluted blood under more mild conditions of concentration and at a slower rate than is current practice in order to obtain an unexpected volumetric modification of at least one of the three-populations of leukocytes, whereby volumetric differential analysis can be accomplished.

21 Claims, 4 Drawing Figures

METHOD FOR THREE-VOLUME DIFFERENTIAL DETERMINATION OF LYMPHOCYTE, MONOCYTE AND GRANULOCYTE POPULATIONS OF LEUKOCYTES

BACKGROUND OF THE INVENTION

This invention concerns methodology and a reagent system for volume differentiation of at least two populations of leukocytes and, more specifically, the classifying and counting of at least three populations of leukocytes (1) a lymphocyte population, (2) a monocyte population, and (3) a granulocyte population which includes neutrophils, eosinophils and basophils, using the Coulter Counter® Model S Plus automated blood counter.

Such data are useful as a screening tool for calling attention to abnormal leukocyte ratios. Abnormal situations identified by this method give information of diagnostic significance and alert the technologist to the need for further study.

Separation of normal human leukocytes by volume distribution utilizing the principle of counting and sizing employed in Coulter Counter® instruments is now applied as a clinical diagnostic method. This method is based on the fundamental property of all living cells to maintain a certain size and shape. Each type of cell in the circulating blood has its own characteristic volume ranging from as small as 3 cubic microns, i.e. 3 fL, for platelets to 650 fL for polymorphonuclear cells. Advanced Coulter Counter® instruments have been designed to make use of this volume differential for the purposes of counting and determining the size distribution of platelets, leukocytes, and erythrocytes in order to detect and monitor pathological states.

Erythrocytes and the lymphoid leukocytes unfortunately overlap considerably in cell sizes, and it is not practical to count one in the presence of the other by size discrimination alone. Traditional practice involves the use of a strong lytic-surfactant reagent that stromatolyses the erythrocytes, reducing them to very small particles or causing membrane solubilization, and strips the cytoplasm from both the lymphoid and the myeloid leukocytes, leaving only the lyse-resistant nuclei to be counted. Since original cell volume is drastically affected and reduced to a minimum, only a single leukocyte population is visible by the usual size distribution analysis.

The Coulter Counter® Model S Plus automated blood cell counter is designed to dilute a sample of whole blood in an isotonic diluent, add a lysing agent, and shortly thereafter begin counting. Thus, a diluent-lysing system must provide erythrocyte lysing kinetics sufficiently rapid to effect complete stromatolysation of the red blood cells (erythrocytes) during the lysing period. In addition, changes in leukocyte volume must be minimal during the data collection step, and ideally should be stable for several minutes. The reagent system must also preserve the integrity of the erythrocyte and platelet number and size distribution, the hemoglobin absorbance spectrum and the total leukocyte count. Finger stick bloods must be stable when prediluted in the isotonic diluent for at least two hours.

In U.S. Pat. No. 3,874,852 (1975) to Coulter Diagnostics, Inc., a formula is included for a composition containing quaternary ammonium salt detergent and potassium cyanide to be employed as a lysing and chromagen-forming reagent for obtaining a single volume leukocyte count and hemoglobin determination in the Coulter Counter® Model S.

In U.S. Pat. No. 4,286,963 to Coulter Electronics, Inc., a lytic diluent for the rapid lysing of red blood cells in whole blood for making a differential determination of lymphoid/myeloid populations of leukocytes, and also measuring hemoglobin by chromagen formation, contains a mixture of an aqueous saline solution of at least one quaternary ammonium salt having surface acting properties, and certain additives such as 2-phenoxyethanol.

In U.S. Pat. No. 4,346,018 to Coulter Electronics, Inc., and in continuing application Ser. No. 395,530 filed July 6, 1982, an isotonic multi-purpose blood diluent and a method for use of this diluent with a lysing reagent system are described for the differential two-volume determination of lymphoid-myeloid populations of leukocytes. An important difference between the two applications is that in claim 1 chlorhexidene diacetate is a named ingredient only in U.S. Pat. No. 4,346,018. This ingredient is also omitted in the preferred embodiment of this application.

To achieve an analysis of the three-volume populations of lymphocyte, monocyte and granulocyte cells in the blood, the leukocyte volume histogram needs to show cleanly separated populations, with little cellular debris, allowing valleys very close to the baseline. Integration of each population will give the relative numbers of the lymphocyte, monocyte and granulocyte cells. The lymphoid population has been demonstrated to contain lymphocytes and small atypical lymphocytes, while the myeloid population contains two subgroups, the monocytes and granulocytes. The granulocytes include neutrophils, eosinophils, and basophils.

SUMMARY OF THE INVENTION

The present invention relates to a method for subjecting a whole blood sample to a reagent system to achieve at least a volumetric differentiation of the monocyte and granulocyte populations. This invention in fact provides a method for classifying and counting three populations of leukocytes namely lymphocyte, monocyte and granulocyte populations, particularly in automatic particle counting systems, such as the automated Coulter Counter® Model S Plus, with only slightly modified programming and an external or internal leukocyte Channelyzer® instrument capability.

The method comprises the steps of supplying a whole blood sample and a predetermined concentration of an isotonically balanced diluent, the diluent being adjusted to a predetermined pH and osmolality, and mixing the sample of whole blood and diluent with a lysing reagent in a predetermined total volume and in such a manner so as to result in the volumetric modification of the individual blood cells of at least one of the populations of leukocytes for a significant period of time to thereby enable the automatic differentiation of three populations.

The reagent system employed in the method of the invention includes a multi-purpose isotonic blood diluent that comprises a mixture of organic buffering means, cell membrane stabilizing means, and a germicidal means, the end volume concentration and total amount of which serve to slow the lytic kinetics of a lysing reagent upon the leukocytes and achieve a differential volume reduction, while stabilizing the traditional hemogram parameters.

The lysing reagent best suited to this invention method is a mixture of an aqueous solution of quaternary ammonium salts having surface active properties, in a volume concentration range and total amount that is effective to give three-leukocyte volume histograms. The lysing agent is hypotonic and therefore tends to combat the shrinkage of the myeloid cells, such shrinkage being well known in the art. Data are presented using standard Coulter Counter ® equipment in conjunction with a Coulter Channelyzer ® and an X-Y plotter. Ancillary calculating and data handling devices are desirable for complete automation, but are not essential to performance of the measurements.

In the preferred commercial embodiment utilizing this invention an alkali metal cyanide is added as the chromagen-forming agent. Other chromagen-forming agents, such as Drabkin's reagent, which contains potassium ferricyanide, potassium cyanide and sodium bicarbonate also may be used.

Unexpectedly, it was discovered that when the conventional lysing reagents and method are modified to give a more mild exposure of the white blood cells in the blood sample to the lysing agent, so that the white blood cells (leukocytes) are not exposed to a high concentration of the lytic agent at any time, i.e. reduce the "lytic shock", the granulocytes are maintained at a higher volume, allowing the visualization and enumeration of a third population, namely the monocytes; i.e. the middle volume region between the lymphocytes and the granulocytes is expanded (freed of granulocytes) sufficiently to allow enhancement of a third population, the monocytes. Therefore, instead of obtaining only a two-population separation of the white cells into lymphoid and myeloid, as is taught by U.S. Pat. No. 4,286,963, U.S. Pat. No. 4,346,018, as shown in FIG. 1A, and continuing application Ser. No. 395,530 already cited, the myeloid cells are separated into two subpopulations, making a total of three populations, namely lymphocytes, monocytes and granulocytes as in FIG. 1B. Furthermore, it was discovered by using this method that the instrument is capable of detecting several types of abnormal blood samples by examination of the positions and relative magnitudes of the peaks and valleys of the histogram, and by the finding of abnormally high percentage of cells in the monocyte region, as well as by abnormal total white counts. Thus the new method has specific clinical utility for the physician.

It is to be appreciated that the practice of this invention does not require both counting and classifying of the white blood cells. It can be used for enhancing either one or both counting and classifying by instrumentation. Moreover, the isotonic diluent and the lysing reagent can be premixed or postmixed to the addition of the blood cells. If postmixed, then the blood sample should not be subject to the full strength of the lysing agent, but should be diluted by the diluent, as taught in the Detailed Description of the Invention.

BRIEF DESCRIPTION OF THE DRAWINGS

FIGS. 1A and 1B comparatively show histograms developed from the same normal blood sample, FIG. 1A utilizing prior art two-population technology and FIG. 1B utilizing the teachings of the present invention to achieve a three-population histogram; and FIGS. 1C and 1D illustrate three-population histograms developed by the present invention from different blood samples.

DETAILED DESCRIPTION OF THE INVENTION

Figure 1:
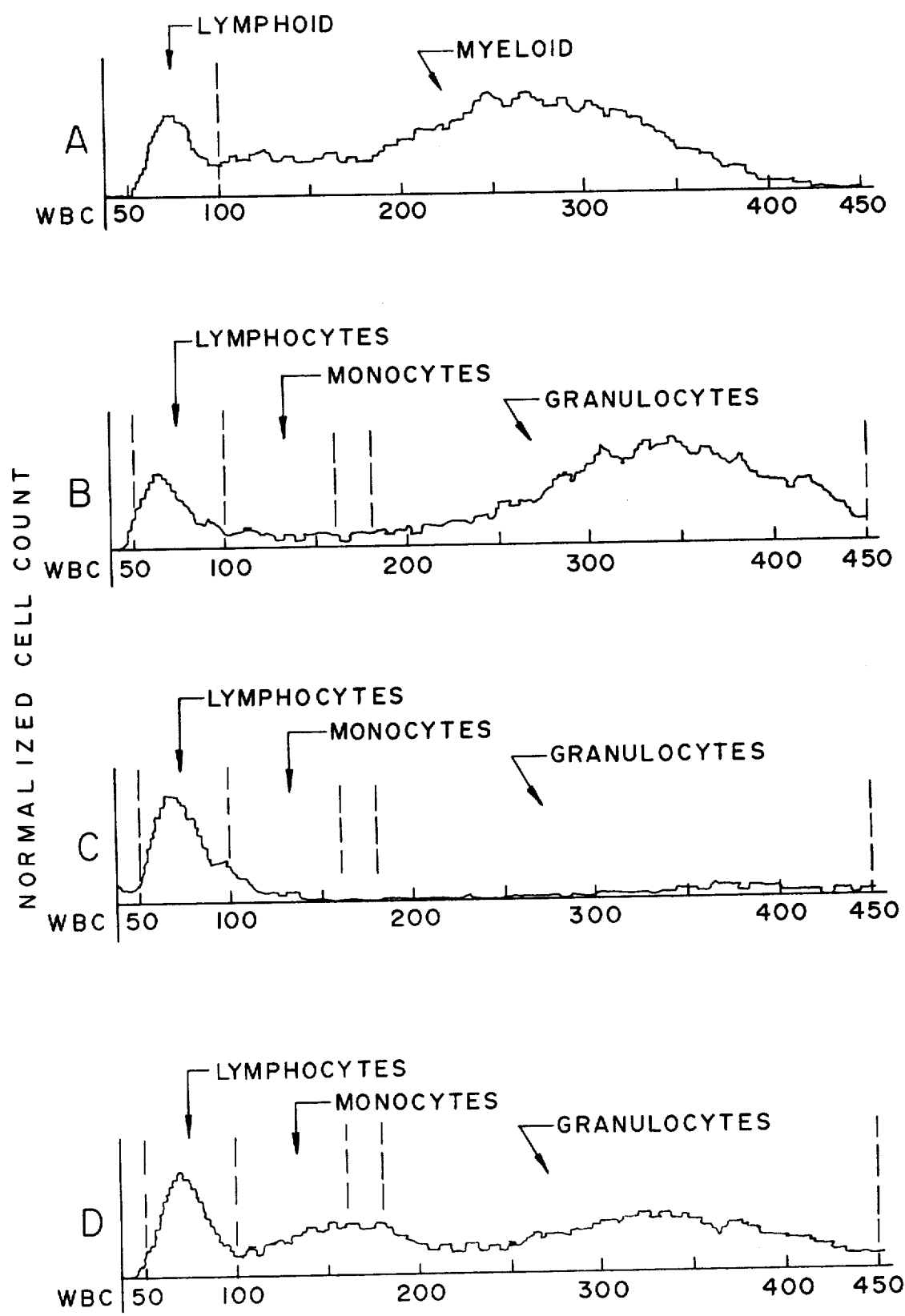
FIGS. 1A through 1D are leukocyte distribution histograms, on the same scale.

The introduction of high speed automated hematology instruments such as the Coulter Counter ® Model S as described in U.S. Pat. No. 3,549,994 resulted in a need for a high speed erythrocyte stromatolysing reagent which gives a clear, stable, reproducible solution. In an instrument of this type, blood is mixed with a conventional diluent, to provide a first dilution, and then mixed with a lysing agent, to provide a second dilution. The mixture remains in the lysing chamber for a short but sufficient amount of time for the erythrocytes or red blood cells to be disintegrated (stromatolysed) and release their hemoglobin. The lysing agent also converts the hemoglobin to a chromagen suitable for measurement. The resulting suspension is passed through sensing apertures in a leukocyte counting bath, wherein the leukocytes or white blood cells are counted and sized electronically. Inasmuch as the ratio of erythrocytes to leukocytes in normal blood is in the vicinity of 1000:1, the erythrocytes must be reduced rapidly to very small fragments, to avoid interference with leukocyte counting. At the same time, the leukocytes must not be destroyed, even though they will shrink in size to a greater or lesser degree.

As discussed above, a quaternary ammonium salt advantageously is employed as a stromatolysing agent, with the virtually instantaneous destruction of erythrocytes to a level avoiding interference with leukocyte sizing and counting. The quaternary ammonium salt is included in aqueous solution in a concentration within the overall range of about 0.5 to 10 percent, and preferably about 1 to 5 percent by weight of the solution, and is mixed with blood previously diluted with a diluent, in a ratio of about 1:11 lysing agent volume to diluted sample volume. It will be understood that a different strength lysing agent may be employed where the initial dilution of the blood sample differs from that described above, in order to provide the same ultimate concentration of reactive lysing agent, or ratio of lysing reagent to whole blood present.

When making a two-volume separation of leukocytes, according to the method of U.S. Pat. No. 4,346,018, it had been observed that the lymphoid-myeloid histograms obtained after lysis on the Coulter Counter ® S Plus instrument consisted of a lymphocyte peak at about 50 to 100 fL, and a myeloid peak, containing monocytes and granulocytes (eosinophils and neutrophils) in the volume range of 100 to 400 fL.

We have discovered and determined by experimentation that the lymphocytes and monocytes are more sensitive than the granulocytes to the lytic agents usually employed. By modifying the kinetics of the lytic method in the Coulter Counter ® S Plus instrument to allow a more mild exposure of the white cells in the blood sample to the lyse reagent, the granulocytes were less "shocked", i.e. subject to a lower or low gradient of lytic shock, and thereby not reduced in size to the extent caused by prior reagent systems and methods. This is accomplished by treating the diluted blood sample with the lyse reagent less rapidly, and when the lyse reagent is in lower concentration than is routinely the case. However, approximately the same amount of lyse reagent is needed in order to ensure complete stromatolysation of the red blood cells. By modification in the kinetics of the method, the lymphocytes are reduced in volume to 50 to 100 fL, the monocytes are reduced to 100 to 160 fL, and the granulocytes demonstrate a volume range of 180 to 450 fL. Consequently, the granulocyte population no longer overlaps the monocyte population and these populations can be enumerated separately. The resulting data must be obtained within a time frame during which time three distinct populations are present.

This is the first time that we have learned how to control the kinetics of the action so as to obtain this important result. In the past, the emphasis has been on the virtually instantaneous destruction of the red blood cells to a level avoiding interference with leukocyte estimation. Herein the emphasis is on discerning the differential volumes of the individual classes of white cells which, unlike the red blood cells, vary in many ways with respect to morphology and the presence of various nuclear forms, volume, as well as function, in health and with disease.

According to this invention a method is provided for the differential determination of lymphocyte, monocyte and granulocyte populations of leukocytes, particularly in automatic counting systems. Hemogram values likewise can be determined. Preferably, the method uses in combination:

(A) A multi-purpose isotonically balanced diluent comprising for example an aqueous solution of:
1. organic buffering means;
2. cell membrane stabilizing means; and
3. germicidal means;
said diluent having a predetermined pH and osmolality; and vided an alkali metal cyanide. Other chromagen-forming agents also can be employed.

The quaternary ammonium salts have the formula:

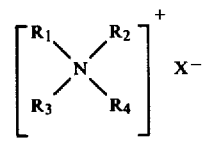

where $R_1$ is a long chain alkyl radical having 10 to 18 carbon atoms; $R_2$, $R_3$, $R_4$ are short chain alkyl radicals having 1 to 6 carbon atoms and $X^-$ is a salt forming radical such as $Cl^-$, $Br^-$, $PO_4^{-3}$ and $CH_3SO_4^-$. In the more useful combinations, the long chain alkyl has 12 to 16 carbon atoms, the short chains are methyl or ethyl, and $X^-$ is chloride or bromide.

The preferred lysing agent employs a combination of dodecyltrimethylammonium chloride, with tetradecyltrimethylammonium bromide and potassium cyanide. Other quaternary ammonium salts that give effective results include hexadecyltrimethylammonium bromide or hexadecyldimethylethylammonium bromide in combination with dodecyltrimethylammonium chloride.

PRIOR ART EXAMPLE

Following the recommended directions which are now public knowledge for volume and flow adjustments of Coulter Counter ® Model S Plus, in order to produce two-volume (lymphoid-myeloid) populations of leukocytes, the following ingredients are employed in the concentrations indicated:

|  | CONCENTRATION PREFERRED | CONCENTRATION RANGE |
|---|---|---|
| DILUENT-U.S. Pat. No. 4,346,018 (col. 3, line 55) | | |
| 1. Procaine hydrochloride | 0.11 g/L | 0.05 to 0.25 g/L |
| 2. N—(2-acetamido)iminodiacetic acid (ADA) | 1.40 g/L | 1.0 to 2.5 g/L |
| 3. Dimethylolurea | 1.00 g/L pH 7.0 ± 0.1 osmolality | 0.5 to 2.5 g/L 320 ± 5 mOs/Kg |
| LYSING AGENT-U.S. Pat. No. 4,346,018 (col. 6, line 20) | | |
| 1. Dodecyltrimethylammonium chloride 50% solution | 60 g/L | 40 to 70 g/L |
| 2. Tetradecyltrimethylammonium bromide | 6 g/L | 4 to 7 g/L |
| 3. Potassium cyanide | 300 mg/L | 250 to 500 mg/L |
| 4. Water | sufficient for one liter | |

(B) a lysing agent which is an aqueous solution of quaternary ammonium salts having surface active properties.

To form a suitable chromagen for hemoglobin determination, as is desired for operation of a Coulter Counter ® Model S Plus instrument, there also can be provided

EXAMPLE 1

Using the same formulation of the diluent as in the Prior Art Example, but a different concentration of the ingredients and doubling the volume of the lysing agent, a three-population histogram can be obtained. For example:

| LYSING AGENT - Three-Population | CONCENTRATION PREFERRED | CONCENTRATION RANGE |
|---|---|---|
| 1. Dodecyltrimethylammonium chloride-50% solution | 35 g/L | 20 to 55 g/L |
| 2. Tetradecyltrimethylammonium bromide | 3.7 g/L | 2 to 6 g/L |
| 3. Potassium cyanide | 150 mg/L | 125 to 250 mg/L |

| LYSING AGENT - Three-Population | CONCENTRATION PREFERRED | CONCENTRATION RANGE |
|---|---|---|
| 4. Water | sufficient for one liter | |

EXAMPLE 2

Using the same formulation of the diluent as in Prior Art Example, but with the following formulation of ingredients for the lysing agent and a doubling of the volume of the lysing agent, a three-population histogram was obtained:

| LYSING AGENT - Three Population | CONCENTRATION PREFERRED | CONCENTRATION RANGE |
|---|---|---|
| 1. Dodecyltrimethyl-ammonium chloride-50% solution | 35 g/L | 20 to 55 g/L |
| 2. Dimethylethylhexadecyl-ammonium bromide | 2.5 g/L | 1 to 6 g/L |
| 3. Potassium cyanide | 150 mg/L | 125 to 250 mg/L |

EXAMPLE 3

Using the same formulation of the diluent as in Prior Art Example, but with the following formulation of ingredients for the lysing agent and doubling the volume of the lysing agent, a three-population histogram was obtained:

| LYSING AGENT - Three Population | CONCENTRATION PREFERRED | CONCENTRATION RANGE |
|---|---|---|
| 1. Dodecyltrimethyl-ammonium chloride-50% solution | 35 g/L | 20 to 55 g/L |
| 2. Hexadecyltrimethyl-ammonium bromide | 2.7 g/L | 1 to 6 g/L |
| 3. Potassium cyanide | 150 mg/L | 125 to 250 mg/L |

The ranges of pH and osmolality of the diluent used for this invention can be broader than shown in the Prior Art Example, for example: pH 7.0±0.4; osmolality 320±50 mOs/Kg.

It is to be appreciated that the alkali metal cyanide, for example in the form of potassium cyanide, is an optional ingredient used to form a chromagen for hemoglobin determination and is not for achieving a three-population differentiating leukocyte histogram.

When using a commercial product which is sold under a trademark, the above formulations are adjusted, as needed, in terms of the purity and exact composition of the commercial product then sold in order to achieve the same results with the instrument system.

Different types of automatic and semiautomatic blood cell analyzing instruments can operate, or be made to operate with different volumes and concentrations of diluents and lytic agents than hereinabove set forth. Differences also can be built into the rate of flow, etc. Such differences also could be developed into Coulter Counter ® instruments of the Model S Plus type and of other models, while at the same time operating under the basic teachings of this invention and its discovery of reducing the lytic shock in such a manner so as to maintain the granulocytes at a higher volume relative to the monocytes and thereby enable the enumeration of the monocytes as a third distinctive population.

As can be seen from the above Examples, the new result of producing a three-population histogram instead of the known two-population histogram is achieved by diluting the commercial lysing agent, sold under the trademark Lyse S ® Plus to about one-half its concentration and then using about twice the volume of the lysing agent. It should be understood that the concentrations of active ingredients in the lysing agent formulations can be altered if the volume of lysing reagent to be used is modified correspondingly, as long as the ratios of the lysing components are maintained within certain limits. For example: 1 part tetradecyltrimethylammonium bromide to 9.5±4 parts dodecyltrimethylammonium chloride-50% solution; or 1 part dimethylethylhexadecylammonium bromide to 14±6 parts dodecyltrimethylammonium chloride-50% solution; or 1 part hexadecyltrimethylammonium bromide to 13±6 parts dodecyltrimethylammonium chloride-50% solution. The "part" or "parts" referred to in this paragraph are measured in grams per liter of the lysing agent, as in Examples 1, 2 and 3 respectively. Also, the ratio of whole blood to active lytic ingredients should be maintained in a certain range. For example: 0.132±0.060 mg tetradecyltrimethylammonium bromide and 1.25±0.60 mg dodecyltrimethylammonium chloride-50% solution is to be added per uL of whole blood. Thus the ratio of whole blood to active lytic ingredients approximates the ratio of 1 uL:1.4 mg. The above values are only examples based on successful formulations, and reasonable deviations therearound would be expected to provide useful results to achieve the goal of the invention.

According to the known operation for the Coulter Counter ® Model S Plus automatic particle counting system, the mixture of whole blood and the isotonic diluent are fed into the white cell counting bath, and the lyse also is added to the same counting bath during a portion of such infeed, for about one-half second. In a preferred form of the new process of this invention the time of lyse feed is increased so that the lytic agent is added to the counting bath for approximately one and one-half seconds of the time that the diluted blood is being fed into the counting bath. For best results, the lyse feed line and the diluted blood feed line are joined together for a significant portion of their length, so as to achieve initial mixing prior to entry into the counting bath. This slower feed of the lysing agent and its longer interaction with the blood, but at a lower concentration, promotes the achievement of the reduction of "lytic shock", i.e. a low or lower gradient of lytic action, which in turn results in the production of three volumes of leukocytes of this invention. In the alternative, the lysing agent and the diluent can be precombined to produce a "lytic diluent" which is used for diluting and lysing the whole blood sample in a manner to achieve the desired low gradient of lytic action.

The reagent system and method of this invention are designed to produce a triphasic size distribution of leukocytes so the pulse height analyzer in the Coulter Counter ® Model S Plus system can identify and count lymphocytes, mononuclear (monocyte) cells and granulocytes.

According to this method the steps of supplying and mixing are accomplished in such a manner that the blood cell volume modification causes the granulocyte population to acquire a volume distribution of larger volume than that of the monocyte population.

The step of mixing the blood and diluent with the lysing reagent employs a significantly weak concentration of the lysing reagent so as to subject the leukocytes to a low gradient of lytic shock. The mixing step also includes feeding the lysing reagent at a significantly slow rate, and/or over a significantly long time duration, which also has the effect of subjecting the leukocytes to a low gradient of "lytic shock".

Following the method of this invention with respect to the slower feed of the lysing reagent and its longer interaction with the blood, but at a lower concentration, it has been found unexpectedly that at least the monocyte and granulocyte populations can be differentially classified and counted by mixing a whole blood sample with the lysing reagent diluted to a predetermined total volume. Thus the final dilution of the whole blood to active lytic ingredients can be attained by diluting only the lytic reagent, rather than by initially adding a diluent to the whole blood prior to mixing it with the lysing reagent according to prior art procedures.

Using the method of this invention, certain abnormal blood samples were seen which lacked granulocytes. These showed lymphocytes in the usual volume range of 50 to 100 fL, monocytes in the volume range of only 100 to 160 fL, and essentially no cells in the range of 180 fL to 450 fL. Samples containing only lymphocytes and monocytes were prepared from normal blood by known physical density separation techniques, and these samples also showed that the monocytes, after lysis, appeared in approximately the same unique volume area.

The described modifications of this invention are not confined to the Coulter Counter ® Model S Plus instruments, but similar considerations are general to other automated instruments and to manual treatment of diluted blood with a lytic reagent in order to reduce or eliminate "lytic shock" and achieve the observed improvement in the volume histograms.

FIG. 1B shows a distribution histogram of a sample of normal blood achieved by the invention, using a Coulter Counter ® Model S Plus and a calibrated Coulter ® Model C-1000 Channelyzer ®. The population on the left contains lymphocytes. The middle population contains mononuclear cells. The population on the right contains granulocytes. The mononuclear cell population includes monocytes and in rare abnormal specimens might also contain blasts and promyelocytes. The granulocyte population includes segmented neutrophils, bands, metameylocytes, eosinophils and basophils.

If the absolute number of cells in the monocyte region is beyond the range, this would be identified by operation of the present invention; then a blood smear slide is prepared and examined to determine what type of abnormal cells are present. In cases of cell population overlap and severely abnormal samples, the operator is alerted by automatic operation of the system using the invention, as will be appreciated with reference to FIGS. 1C and 1D.

Dilution of a lysing agent useful for obtaining the two-volume, lymphoid-myeloid population to about one-half the concentration, doubling the lyse volume, modifying the concentration ratios of the active ingredients, and retarding the rate of lyse addition widens the valley in the volume range above the lymphocytes during a time frame sufficiently long to allow the third population, the monocytes, to be quantified by the automatic particle counter.

These factors were not present in prior known reagent systems and methodology to allow sufficient enhancement of the third population, which is very small in number.

It is substantially the lowered concentration gradient of the lysing agent being dispensed into the dilute blood suspension that gives rise to the unexpected result of the third population. The modified reagent and dispensing method exposes the cells to a much lower lytic concentration gradient, thus slowing the lysing kinetics and maintaining the granulocyte population at a larger volume, allowing detection and enumeration of a third population, namely monocytes.

The third population has been identified as monocytes by:

a. correlation with stained smears and manual differentials,
b. use of lymphocyte/monocyte cell preparations to demonstrate the position of the monocyte population after lysis, and
c. sorting monocytes from blood samples using an EPICS ® V flow cytometer and subsequently running these cells through the Coulter Counter ® S Plus system modified according to this invention and noting the position in the histogram.

Leukocyte fractions containing nearly pure lymphocytes, or monocytes, or neutrophils, or eosinophils were prepared by density gradient separations and these purified samples were combined with "base" blood to make artificially enriched whole blood for examining the leukocyte histograms as compared to manual differential counts. These leukocyte fraction enriched samples and normal samples were examined by the Coulter Counter ® S Plus system and spun films were made for manual differential counts. The Coulter Counter ® S Plus had been modified to calculate lymphocyte percent in the size range 40 to 103 fL, monocytes from 103 to 160 fL and granulocytes above 160 fL. Changes had also been made in the concentration of some active ingredients of the lysing reagent.

A normal whole blood specimen size distribution histogram is shown in Table 1. The estimates of the percentages of the different cell types as given by the instrument and by the manual differential count method are included in Table 1.

TABLE 1

A comparison of the numerical calculation obtained from the automated modified lysing method of the invention with the manually read differential count from a Wright's stained blood smear slide (standard method) of a normal blood sample.

| | Differential Count % Coulter Counter ® | |
|---|---|---|
| | S Plus | Manual |
| Lymphocyte | 21.7 | 28 |
| Monocyte | 5.7 | 6 |
| Neutrophil | N | 63 |
| Eosinophil | E | 4 |
| Basophil | B | 0 |
| | N + E + B = 72.6 | |

A lymphocyte-monocyte enriched specimen was prepared by the standard Ficoll-Hypaque technique. The leukocytes were washed with SBSS and added to autologous whole blood. The size distribution figures for the instrument and manual differential estimates of the percentages of the principal cell types are shown in Table 2.

TABLE 2

| Lymphocyte/monocyte enrichment | | |
|---|---|---|
| | Differential Count % Coulter Counter ® | |
| | S Plus | Manual |
| Lymphocyte | 45.5 | 42 |
| Monocyte | 17.1 | 18 |
| Neutrophil | N | 34 |
| Eosinophil | E | 5 |
| Basophil | B | 1 |
| | N + E + B = 40.4 | |

In normal persons, the cells falling into the volume window between the lymphocytes and granulocytes comprise the monocyte population. The red blood cells are completely stromatolysed, and the red blood cell and platelet counts are essentially the same as in known methods.

In abnormal cases, however, there is occasionally a rise in the "monocyte" population due to blastic or other immature cell species which can be observed by microscopic examination. The monocyte population may be greatly enhanced by the presence of these cells which will be found in the monocyte region of the white cell histogram. This can be demonstrated, for example, by correlating the leukocyte size distribution histograms with manual differential counts observed on whole blood dispersed on glass slides and stained.

The instrument operating according to this invention is capable of detecting severely abnormal blood samples by examination of the positions and relative magnitudes of the peaks and valleys of the histogram, by abnormally high percentage of cells in the monocyte region, and by abnormal total white counts.

Certain types and stages of leukemias are characterized by the presence of very immature cells known as "blasts", which are not found in normal or most abnormal bloods. These blasts are identified partially by their very large size on blood slides; however, they are apparently very sensitive to the lyse and are found in the volume range of 80 to 150 fL, overlapping the lymphocyte and monocyte ranges and resulting in a broad peak in the range without the typical lymphocyte/monocyte "valley" at 100 fL usually found. Such specimens are generally easily detected by the instrument because of the unusual histogram and the often greatly elevated total white blood cell counts.

Blood samples which have been damaged by being excessively aged, subjected to unusually high temperature, etc., will likewise give abnormal histograms readily recognizable by a trained observer and by the computer within the instrument.

FIGS. 1A and 1B comparatively show the Leukocyte Distribution Histograms of the same sample on the Coulter Counter ® Model S Plus automated blood cell counter, which in FIG. 1A results from using the reagent system of U.S. Pat. No. 4,346,018, and FIG. 1B results from following the reagent system and method of the present invention.

FIG. 1C is the histogram from a patient with severe leukopenia. Very few cells are present in the granulocyte zone. The lymphocyte peak tails into the mononuclear region. The stained blood slide showed an occasional multi-lobed neutrophil, normal numbers of mature lymphocytes and several blasts.

FIG. 1D shows a lymphocyte peak which appears normal. There is a marked elevation of the mononuclear region as well as the granulocyte zone.

While certain representative embodiments and details have been shown for the purpose of illustrating the invention, various changes and modifications can be made therein without departing from the scope of the invention as defined in the appended claims.

We claim:

1. A method for the volumetric differentiation of leukocytes into at least two populations which are identified as monocytes and granulocytes, respectively, from a whole blood sample, using an automatic particle analyzing system, said method comprising the steps of:
   I. supplying, for use by the analyzing system for its mixing and analyzing, the whole blood sample and a volume of an isotonically balanced blood diluent; and
   II. mixing the whole blood sample and the diluent by the analyzing system with a therein supplied lysing reagent in such a manner that the lysing reagent is at a significantly weak concentration and is supplied at a significantly slow rate, so as to subject the leukocytes to a low gradient of lytic shock, so as to result in the volumetric modification of the individual blood cells of at least one of the populations of leukocytes for a significant period of time to thereby enable the automatic differentiation of the leukocyte populations by the analyzing system;
   the lysing reagent comprising a mixture of an aqueous solution of quaternary ammonium salts having surface acting properties.

2. The method of claim 1 wherein the ratio of whole blood to active lytic ingredients in said lysing reagent approximate the ratio of 1 uL:1.4 mg.

3. The method of claim 1 in which said steps of supplying and mixing are accomplished in such a manner that the blood cell volume modification causes the granulocyte population to acquire a volume distribution of larger volume than that of the monocyte population.

4. The method of claim 1 further including the step of, at least one of, counting and classifying the differentiated populations.

5. The method of claim 1 wherein the whole blood sample is at least partially diluted with the blood diluent before mixing with the lysing reagent.

6. The method of claim 1 wherein the lysing reagent is at least partially diluted with the blood diluent before mixing with the whole blood sample.

7. The method of claim 1 wherein the lysing reagent further comprises means for forming a suitable chromagen for hemoglobin determination.

8. The method of claim 7 wherein said chromagen forming means is an alkali metal cyanide.

9. The method of claim 1 wherein said quaternary ammonium salts are a mixture of dodecyltrimethylammonium chloride and hexadecyltrimethylammonium bromide.

10. The method of claim 9 wherein said dodecyltrimethylammonium chloride and said hexadecyltrimethylammonium bromide measured in grams per liter are present in the approximate ratio of 13±6:1.

11. The method of claim 1 wherein said quaternary ammonium salts are a mixture of dodecyltrimethylammonium chloride and dimethylethylhexadecylammonium bromide.

12. The method of claim 11 wherein said dodecyltrimethylammonium chloride and said dimethylethylhexadecylammonium bromide measured in grams per liter, are present in the approximate ratio of 14±6:1.

13. The method of claim 1 wherein the whole blood sample contains lymphocytes, and the volumetric modification of the blood cells enables three population differentiation.

14. The method of claim 13 wherein the volumetric modification of the blood cells causes the monocyte population to be positioned volumetrically between the lymphocyte and granulocyte populations.

15. The method of claim 1 wherein the diluent comprises a mixture of: (1) buffering means, (2) cell membrane stabilizing means, and (3) germicidal means; the end volume concentration and total amount of which serve to slow the lysing kinetics upon at least one of the leukocyte populations.

16. The method of claim 15 wherein said buffering means is N-(1-acetamido)iminodiacetic acid (ADA); said cell stabilizing means is Procaine hydrochloride; and said germicidal means is dimethylolurea.

17. The method of claim 15 wherein said diluent has a pH of about 7.0±0.4 and an osmolality of about 320±50 mOs/kg.

18. The method of claim 1 wherein said quaternary ammonium salts are a mixture of dodecyltrimethylammonium chloride and tetradecyltrimethylammonium bromide.

19. The method of claim 18 wherein said dodecyltrimethylammonium chloride is present in a concentration range of 20 to 55 g/L and said tetradecyltrimethylammonium bromide is present in a concentration of 2 to 6 g/L.

20. The method of claim 18 wherein said dodecyltrimethylammonium chloride and said tetradecyltrimethylammonium bromide measured in grams per liter, are present in the approximate ratio of 9.5±4:1.

21. A method for the volumetric differentiation of at least the monocyte and granulocyte populations obtained from a whole blood sample, said method comprising the steps of:

supplying and mixing the whole blood sample and a lysing reagent, the lysing reagent is at a significantly weak concentration and is supplied at a significantly slow rate so as to result in a low gradient of lytic shock and thereby the volumetric modification of the individual blood cells of at least one of the populations of monocytes and granulocytes for a significant period of time to thereby enable the volumetric differentiation of these populations.

* * * * *